(12) United States Patent
Karmaker

(10) Patent No.: US 7,997,901 B2
(45) Date of Patent: Aug. 16, 2011

(54) FIBER REINFORCED COMPOSITE POST

(75) Inventor: Ajit Karmaker, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 442 days.

(21) Appl. No.: 12/054,947

(22) Filed: Mar. 25, 2008

(65) Prior Publication Data

US 2009/0246738 A1    Oct. 1, 2009

(51) Int. Cl.
*A61C 5/08* (2006.01)
(52) U.S. Cl. ........................ 433/224; 433/220
(58) Field of Classification Search ................. 433/220, 433/224, 212.1, 180
See application file for complete search history.

(56) References Cited

U.S. PATENT DOCUMENTS

| | | | |
|---|---|---|---|
| 3,066,112 A | 11/1962 | Bowen | |
| 3,179,623 A | 4/1965 | Bowen | |
| 3,194,784 A | 7/1965 | Bowen | |
| 3,751,399 A | 8/1973 | Lee, Jr. et al. | |
| 3,926,906 A | 12/1975 | Lee, II et al. | |
| 4,544,359 A | 10/1985 | Waknine | |
| 4,547,531 A | 10/1985 | Waknine | |
| 4,717,341 A | 1/1988 | Goldberg et al. | |
| 4,894,012 A | 1/1990 | Goldberg et al. | |
| 5,276,068 A | 1/1994 | Waknine | |
| 5,564,929 A | 10/1996 | Alpert | |
| 5,797,748 A | 8/1998 | Reynaud et al. | |
| 5,846,640 A * | 12/1998 | Vallittu | 428/306.6 |
| 5,890,904 A * | 4/1999 | Reynaud et al. | 433/220 |
| 5,919,044 A | 7/1999 | Sicurelli, Jr. et al. | |
| 6,030,220 A | 2/2000 | Karmaker et al. | |
| 6,039,569 A | 3/2000 | Prasad et al. | |
| 6,183,253 B1 * | 2/2001 | Billet et al. | 433/81 |
| 6,267,597 B1 * | 7/2001 | Kim | 433/224 |
| 6,371,763 B1 * | 4/2002 | Sicurelli et al. | 433/220 |
| 6,402,519 B1 * | 6/2002 | Nordin | 433/220 |
| 6,439,890 B1 | 8/2002 | Karmaker et al. | |
| 7,235,290 B2 | 6/2007 | Vallittu et al. | |
| 7,318,726 B2 * | 1/2008 | Nordin | 433/224 |
| 7,673,550 B2 * | 3/2010 | Karmaker et al. | 87/1 |
| 2007/0207444 A1 | 9/2007 | Reynaud et al. | |
| 2008/0250974 A1 * | 10/2008 | Jia | 106/35 |

* cited by examiner

*Primary Examiner* — Ralph A Lewis
(74) *Attorney, Agent, or Firm* — Wood, Herron & Evans, LLP

(57) ABSTRACT

A fiber-reinforced composite post having an inner core section or rod fabricated of fibers impregnated in a resin matrix and an out sheath of fibers arranged in the form of a mesh. The sheath comprises an interior and an exterior surface, whereby the interior surface is attached to and embedded in the resin matrix of the rod and the exterior surface has dry, unimpregnated fibers.

9 Claims, 3 Drawing Sheets

FIBER REINFORCED COMPOSITE POST

BACKGROUND

This invention relates to fiber-reinforced composite posts for dental and endodontic applications and more particularly to fiber-reinforced composite posts having good bonding properties.

Dental posts must adhere well to other materials, such as other resins or composites, or to living tissue, such as bone. There are a variety of dental posts on the market today, including ceramic, metal and fiber-reinforced composite posts. U.S. Pat. No. 6,439,890 is directed to a fiber-reinforced composite dental post comprising a plurality of frustoconical sections arranged coaxially along the longitudinal axis of the rod. The frustoconical or jagged sections provide a rough surface to promote chemical bonding as well as mechanical anchors, resulting in a better retention of the post.

U.S. Publication No. 200070207444 is also directed to a fiber-reinforced dental post containing a central core of fibers embedded in a resin matrix and a sheath surrounding the core, wherein the sheath is free of fibers. The post includes a silane coating to improve the adhesion of the post to the bonding agent when inserting the post into the patient's root.

U.S. Pat. No. 5,797,748 is directed to a dental post having a central core and a sheath surrounding the central core, wherein the central core is made of at least one bunch of fibers and the core is wrapped by a sheath having at least one layer of oriented, isotropic or non-isotropic fibers. The fibers in the core and the fibers in the sheath are embedded in a curable resin. In order to facilitate adhesion of the post with cement, macro-retentions may be created on the surface of the post, particularly by machining and more particularly by turning or slicing. In order to avoid deteriorating the sheath, it must be overmolded with a resin envelope of small thickness, and the macro-retentions are created on the resin envelope.

Thermoplastic materials are generally ductile, but lack adequate bonding to the resin/cement core materials, which are generally made with dimethacrylic monomers. U.S. Pat. No. 7,235,290, which is hereby incorporated by reference, is directed to a method of making a fiber-reinforced composite material with improved bonding. The outer layer of fibers is exposed by dissolving the outer layer of matrix resin that holds the outer layer of fibers. The dissolution step in this process can weaken the interface between the matrix and the outer layer of fibers, affecting the overall strength of the final product.

It is therefore an object of the invention to provide a dental post fabricated of a fiber-reinforced composite material that is able to bond well to other materials, such as resins and composites and also to living tissue, such as bone. It is a further object of the invention to provide a fiber-reinforced composite dental post that exhibits good mechanical properties.

SUMMARY OF THE INVENTION

These and other objects and advantages are accomplished by a fiber-reinforced composite post having an inner core section or rod fabricated of fibers impregnated in a resin matrix and an outer sheath of fibers arranged in the form of a mesh. The sheath comprises an interior and an exterior surface, whereby the interior surface is attached to and embedded in the resin matrix of the rod and the exterior surface has dry, unimpregnated fibers.

In an embodiment of a method of manufacturing the dental post herein, a fiber-reinforced composite rod is provided or fabricated of longitudinally extending fibers disposed in a resin matrix material, with or without fillers added. The resin matrix material is cured to provide a solid rod. A dry sheath of mesh fibers are applied on and around a fiber-reinforced composite rod. Heat and pressure are applied simultaneously to attach the sheath to the rod. The sheath is adhered to the rod and left dry and unimpregnated.

DETAILED DESCRIPTION

Figure 1:
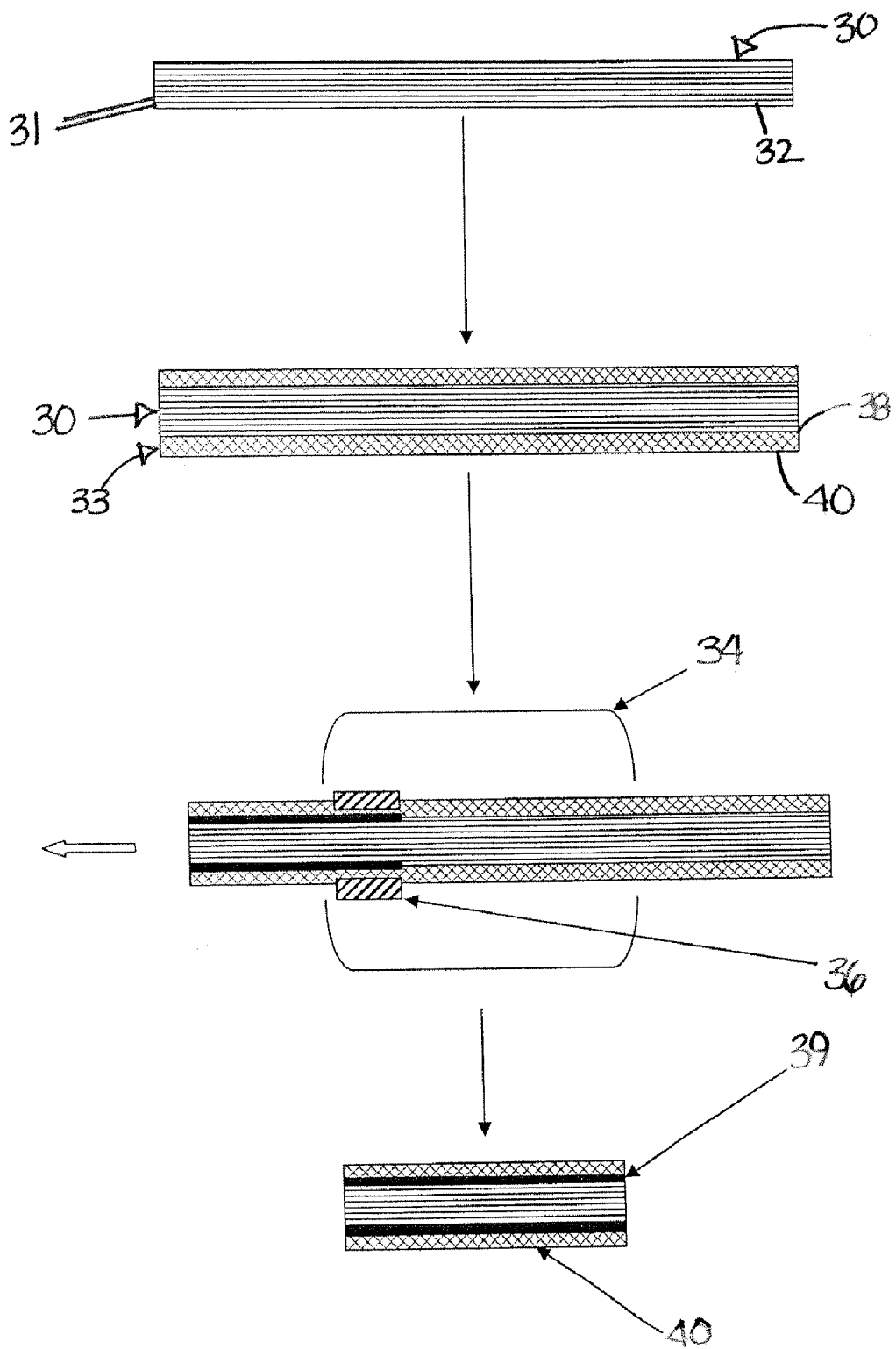
FIG. 1 shows the process of manufacturing a dental post in accordance with the present invention.

As will be appreciated, the present invention provides a fiber-reinforced composite having a rod of longitudinally extending fibers disposed in a composite and a sheath of woven or braided fibers enveloping the rod. The fiber-reinforced composite is fabricated by forming a rod of longitudinally extending fibers impregnated in a resin. Fillers may also be included in the resin for further reinforcement. The sheath may be a sleeve of material that is applied around the rod such that it envelops the rod. The final product is a rod of longitudinally extending fibers disposed in, or impregnated with, a resin matrix material, which rod is surrounded by a sheath of woven or braided fibers. The sheath is left dry and is not impregnated with a resin matrix material. The sheath and rod are held together by the resin matrix material in the rod.

Fibers in the fiber-reinforced composite and in the sheath may include glass, ceramic, metal, carbon, graphite, polymeric such as cellulose, polyamide, aramid, polyester, polyaramid, acrylic, vinyl and modacrylic, polyolefin, polytetrafluorethylene, mixtures thereof, as well as other fibers known in the art. One preferred version of the rod is comprised of unidirectional microfilamentous glass fibers bundled in a resin matrix.

Resin materials may include those known in the art of dental materials, including, but not limited to, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates (hereinafter abbreviated to PUDMA), and the like. It is preferred that the resin matrix is a thermoplastic material.

Preferred polymeric matrix materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine (which are herein incorporated by reference). An especially preferred methacrylate monomer is the condensation product of bisphenol A and glycidyl methacrylate, 2,2'-bis[4-(3-methacryloxy-2-hydroxy propoxy)-phenyl]-propane (hereinafter abbreviated "BIS-GMA").

The polymer matrix, which typically includes polymerization initiators, polymerization accelerators, ultra-violet light absorbers, anti-oxidants, fluorescent whitening agents, free radical initiators, and/or other additives well known in the art, may be visible light curable, self-curing, dual curing, or vacuum, heat, or pressure curable compositions, as well as any combination thereof. Heat and pressure or vacuum curable compositions include a heat cure initiator such as benzoyl peroxide, 1,1'-azobis(cyclohexanecarbo-nitrile) or other free radical initiators. The preferred polymeric matrix is a light and heat curable matrix, wherein light effects partial cure of the polymer matrix, while final curing is by heat under controlled atmosphere.

Examples of fiber reinforced composite materials comprising the reinforcing component in a polymeric matrix material are disclosed in U.S. Pat. Nos. 4,717,341 and 4,894,012 to Goldberg et al., U.S. Pat. No. 6,039,569 to Prasad et al., U.S. Pat. No. 6,030,220 to Karmaker et al., U.S. Pat. No. 5,564,929 to Alpert, and U.S. Pat. No. 5,919,044 to Sicurelli, Jr. et al., all of which are hereby incorporated by reference.

In order to enhance the bond between the fibers and polymeric matrix, thereby enhancing the reinforcing effect, the fibers may be silanized or otherwise treated such as by grafting functional monomers or by surface modification by corona, high voltage flame or plasma treatment, to obtain proper coupling between the fibers and the resin matrix. Silanization renders the fibers hydrophobic, reducing the water sorption and improving the hydrolytic stability of the composite material, renders the fibers organophilic, improving wetting and mixing, and bonds the fibers to the polymeric matrix. Typical silane is A-174 (p-methacrylate propyl trimethoxy silane), produced by OSI Specialties, New York.

Fillers having an aspect ratio $\geq 1.0$ may be present in addition to or instead of fibers in an amount up to about 80 wt %, and preferably about 70 wt %. If fibers are present, the amount of filler is less than about 30 wt % of one or more fillers known in the art and used in dental restorative materials. Suitable fillers include those capable of being covalently bonded to the polymeric matrix itself or to a coupling agent that is covalently bonded to both. Fillers include silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania, among other conventional fillers such as those disclosed in commonly assigned U.S. Pat. Nos. 4,544,359 and 4,547,531 to Waknine (which are incorporated herein by reference), while possible coupling agents include silanes, zirconates, and titanates.

The core or rod is formed of fiber-reinforced composite material. The materials described above, polymeric materials, resins and fibers, are useful for this embodiment as well. The rod is formed by methods known in the art, such as, but not limited to, matched die processes, autoclave molding, resin injection molding (RIM), sheet, dough and bulk molding, press molding, injection molding, reaction injection molding, resin transfer molding (RTM), compression molding, open molding, hand rolling, dipping and rolling, pressing, extrusion, pultrusion and filament winding. During the manufacturing process, the fiber-reinforced composite is preferably cured to provide a rod-shaped unit or main body which can modified by grinding, cutting, milling or other known shaping means. It is preferable that the rod is fully cured.

A sheath of fibers is then applied to the fully cured rod. The sheath is fabricated using a plurality of fibers and interlacing, braiding, weaving or other method of intertwining to provide a sheath of intertwined or mesh of fibers. The fibers are held together by being woven, braided or interlaced together. It is also possible to procure already-woven fabric and prepare a sheath with the fabric.

The sheath of fibers is applied to the rod by wrapping around or sliding over the rod to encase or envelop the rod. In order to bond the fibers to the rod, heat is applied to soften the resin matrix at the surface of the rod. The heating temperature will be dependent upon the melting or softening temperature of the resin matrix in the fiber-reinforced composite rod. It is important that the heating temperature is not higher than the softening temperature of the fibers used in the sheath. Bonding of the sheath to the rod occurs when the resin matrix softens. Pressure is simultaneously applied during the heating step to assist in the bonding of the fibers in the sheath to the resin matrix in the rod.

It is possible that the rod with sheath thereon is pulled through a heating chamber containing a die, compression roll or other pressure application device. The die or roll is stationary in the chamber and the rod with sheath is pulled through the die or roll and pressure is applied as it is pulled through. Alternately, the rod with sheath is stationary, and the heat and pressure are moved along the rod and sheath to carry out the heating and pressure application step. It is possible that other heating and pressure devices in the art may also be used. Thereafter, the rod and sheath are cooled. Since the outer fibers in the sheath are uncoated, there is no need to dissolve any resin matrix material thereon. Thus, there is no weakening of the matrix or the fibers from any type of solvent.

As a result of the manufacturing process, a part of the fibers in the sheath become embedded in the resin matrix of the rod and the remainder or most likely fibers of the outer surface remain dry. The dry fibers in the sheath provide a means for adhering to another material, such as a cement, resin, composite or body tissue. It is possible that the dry fibers project out from the surface of the sheath and the rod.

In another aspect of this invention, it is preferable that glass filament fibers be used in the rod and in the sheath, since these fibers have a softening point in the range of about 700 to about 1100° C., which is much higher than most resins employed herein. Accordingly, there is less need to be concerned with the melting of the fibers during the heating step. Depending upon the resin and fibers used herein, the heating range can vary from about 100 to about 350° C.

Figure 2:
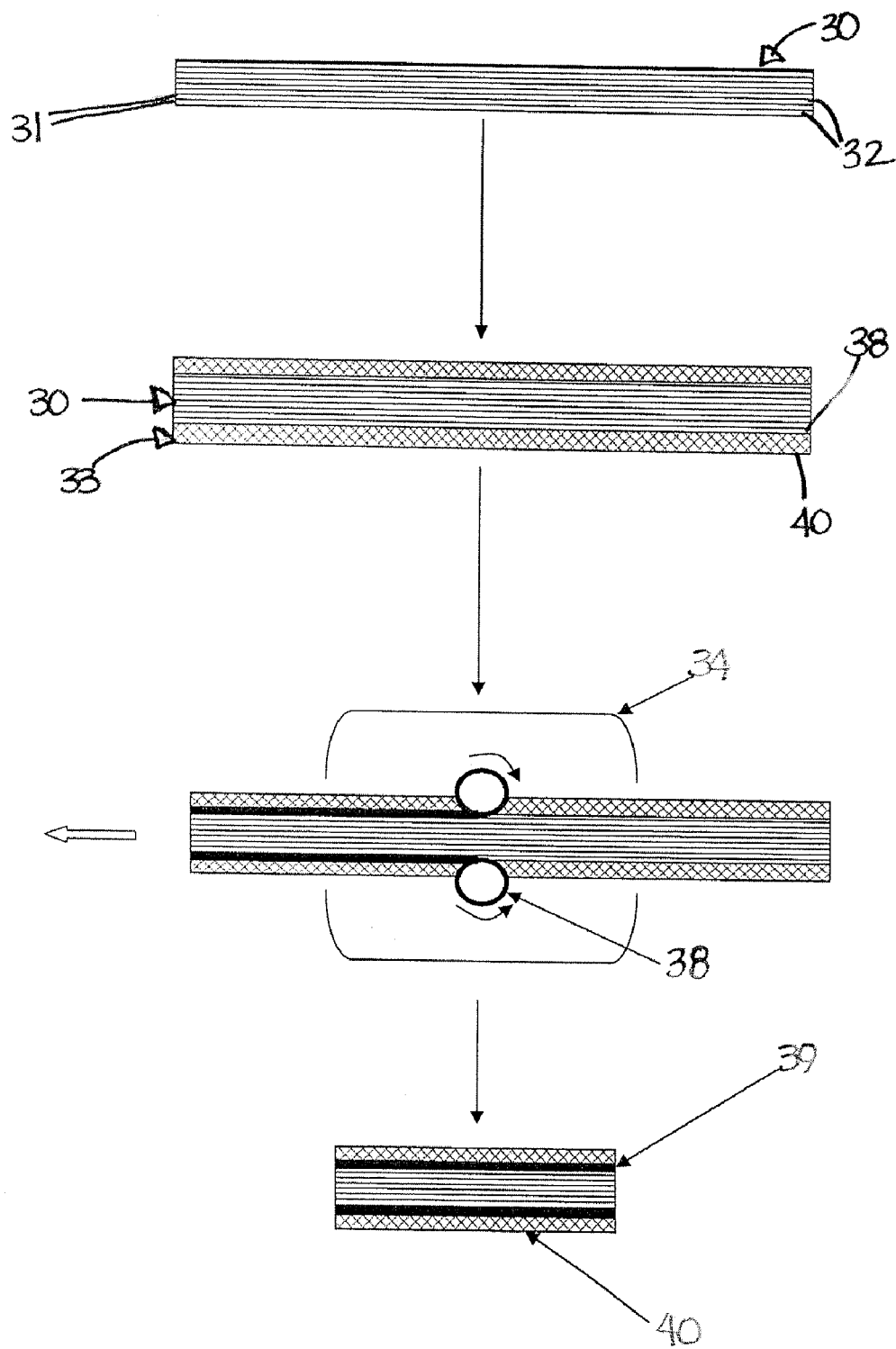
FIG. 2 shows an alternate embodiment of the process of manufacturing a dental post in accordance with the present invention.

FIGS. 1 and 2 illustrate the steps involved in manufacturing the materials herein. In the first step, a fiber-reinforced composite rod 30 is provided, which has been prepared by pultrusion or other process wherein fibers 31 are impregnated with a resin material 32 and cured. In the second step, a sheath 33 of unimpregnated fibers is applied onto rod 30. Next, the rod with sheath thereon is sent through a heating chamber 34. Simultaneously, pressure is applied to the sheath through the use of a die 36, shown in FIG. 1, or a compression roll 38, shown in FIG. 2. The heat and the pressure fuse the internal side 38 of sheath 32 to rod 30 to form an embedded layer 39 of fibers embedded in the matrix resin. The exterior side 40 of sheath 33 remains dry. The dry mesh or fibers are optimal for bonding to resin, composite or other material.

Figure 3:
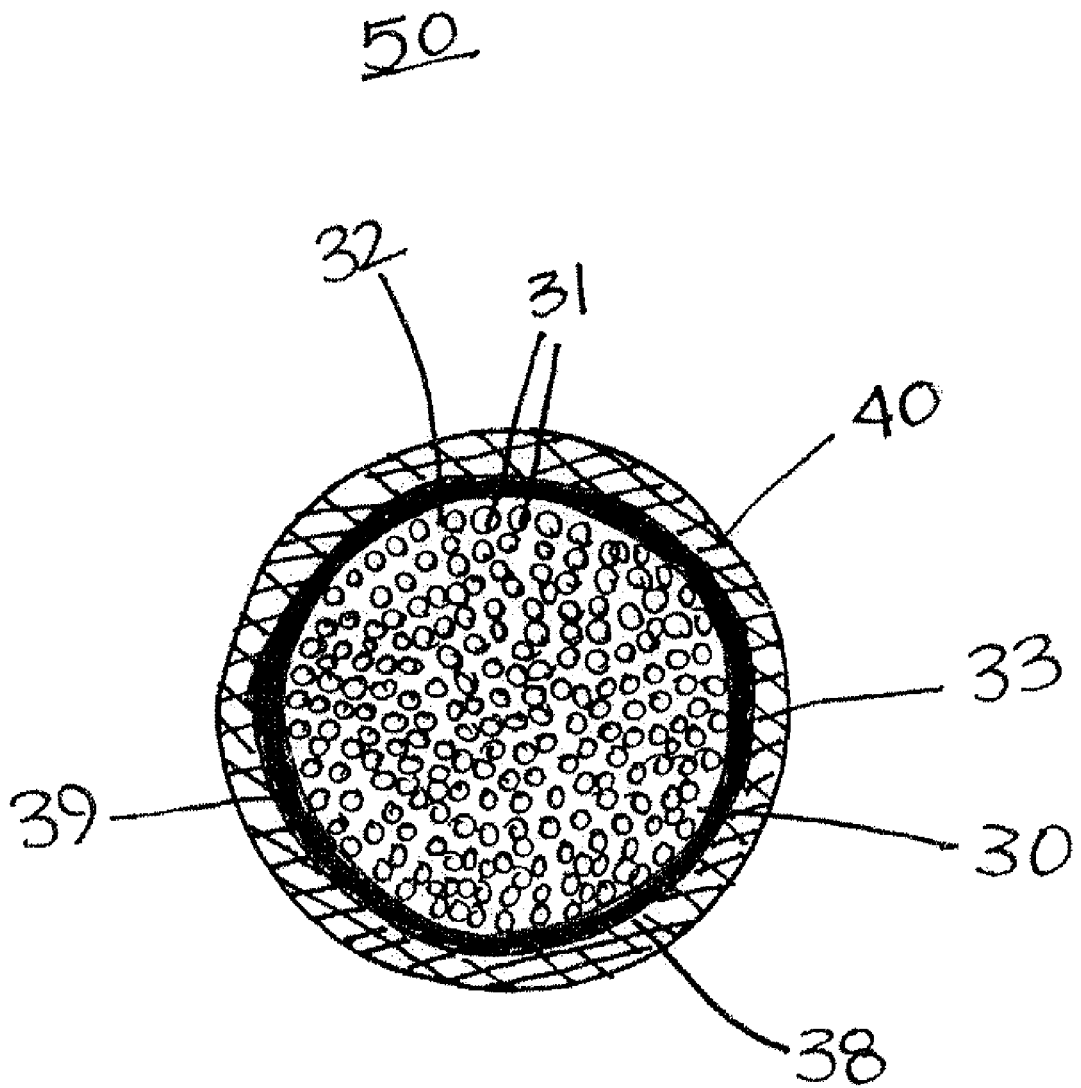
FIG. 3 shows a dental post made in accordance with the manufacturing processes shown in FIGS. 1 and 2.

FIG. 3 shows a finished post 50 fabricated using the manufacturing processes illustrated in FIGS. 1 and 2. Post 50 includes a core 30 and outer sheath 33. Core 30 is fabricated of resin 32 impregnated with fibers 31. Sheath 33 has an interior side 38 and an exterior side 40. The interior side 38 attaches to resin matrix 32 in core 30 to form a fused interface or layer 39 between core 30 and sheath 33.

Fibers may be present in the core or rod material in an amount from about 10 to about 90% by weight of the resin matrix material and preferably about 20 to about 85% of the resin matrix material, and more preferably about 30 to about 80% of the resin matrix material.

As will be appreciated, the present invention provides a fiber-reinforced composite dental post having good strength and good adhesion to other materials, particularly bonding agents for bonding to a root canal.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of forming a fiber-reinforced composite post for dental or endodontic use comprising:
   providing a fiber-reinforced composite rod having a first plurality of fibers impregnated in a resin matrix;
   applying a sheath on the fiber-reinforced composite rod, wherein the sheath comprises a second plurality of fibers arranged in a mesh, wherein the mesh has an interior surface and an exterior surface, wherein the second plurality of fibers arranged in the mesh are dry and unimpregnated to provide a fiber-reinforced composite rod encased in a dry sheath of mesh fibers;
   applying heat and pressure simultaneously to the fiber-reinforced composite rod encased in the dry sheath of mesh fibers;
   whereby the interior surface of the mesh becomes embedded in the resin matrix and the exterior surface of the mesh remains dry and unembedded.

2. The method of claim 1 wherein the heat is applied in the range of from about 100 to about 350° C.

3. The method of claim 1 wherein the pressure is applied with the application of a compression roll or a die.

4. The method of claim 1 wherein the resin matrix material comprises acrylics, methacrylics, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates ("PUDMA"), the condensation product of bisphenol A and glycidyl methacrylate, 2,2'-bis[4-(3-methacryloxy-2-hydroxy propoxy)-phenyl]-propane ("BIS-GMA"), hexanediol dimethacrylate ("HDDMA"), 1,6-bis(methacrylethyloxy carbonylamino)trimethyloxane ("UDMA") or a mixture thereof.

5. The method of claim 1 wherein the first plurality and second plurality of fibers comprise the same material.

6. The method of claim 1 wherein the first plurality of fibers comprise glass, ceramic, metal, carbon, graphite, polymeric, cellulose, polyamide, aramid, polyester, polyaramid, acrylic, vinyl, modacrylic, polyolefin, polytetrafluorethylene or mixtures thereof.

7. The method of claim 1 wherein the second plurality of fibers comprise glass, ceramic, metal, carbon, graphite, polymeric, cellulose, polyamide, aramid, polyester, polyaramid, acrylic, vinyl, modacrylic, polyolefin, polytetrafluorethylene or mixtures thereof.

8. The method of claim 1 further comprising functionalizing the dry and unembedded fibers with silane, titanate, zirconate and/or aluminate.

9. The method of claim 1 wherein the rod has a longitudinal dimension and a lateral dimension and wherein the first plurality of fibers is aligned substantially along the longitudinal dimension of the rod.

* * * * *

UNITED STATES PATENT AND TRADEMARK OFFICE
CERTIFICATE OF CORRECTION

| | | |
|---|---|---|
| PATENT NO. | : 7,997,901 B2 | Page 1 of 1 |
| APPLICATION NO. | : 12/054947 | |
| DATED | : August 16, 2011 | |
| INVENTOR(S) | : Ajit Karmaker | |

It is certified that error appears in the above-identified patent and that said Letters Patent is hereby corrected as shown below:

Title page, Item (57) Abstract, line 2, "an out sheath" should read --an outer sheath--.

Column 2, line 3, "fibers are applied" should read --fibers is applied--.

Column 3, line 56, "which can modified" should read --which can be modified--.

Signed and Sealed this
Twenty-fifth Day of October, 2011

David J. Kappos
*Director of the United States Patent and Trademark Office*